United States Patent
Griffin et al.

(10) Patent No.: US 9,187,716 B2
(45) Date of Patent: Nov. 17, 2015

(54) STRUCTURED SURFACTANT SYSTEM

(75) Inventors: James F. Griffin, Jackson, NJ (US); Stewart A. Warburton, West Windsor, NJ (US); Tobias Johannes Futterer, Princeton, NJ (US)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 13/068,388

(22) Filed: May 10, 2011

(65) Prior Publication Data

US 2011/0280822 A1  Nov. 17, 2011

Related U.S. Application Data

(63) Continuation of application No. 11/903,999, filed on Sep. 25, 2007, now abandoned.

(60) Provisional application No. 60/847,211, filed on Sep. 26, 2006.

(51) Int. Cl.
| | |
|---|---|
| *C11D 1/72* | (2006.01) |
| *C11D 9/00* | (2006.01) |
| *C11D 3/04* | (2006.01) |
| *A61K 8/02* | (2006.01) |
| *A61K 8/20* | (2006.01) |
| *A61K 8/46* | (2006.01) |
| *A61K 8/73* | (2006.01) |
| *A61Q 5/02* | (2006.01) |
| *A61Q 19/10* | (2006.01) |
| *C11D 1/10* | (2006.01) |
| *C11D 1/12* | (2006.01) |
| *C11D 1/28* | (2006.01) |
| *C11D 1/37* | (2006.01) |
| *C11D 1/83* | (2006.01) |
| *C11D 1/94* | (2006.01) |
| *C11D 17/00* | (2006.01) |

(52) U.S. Cl.
CPC .............. *C11D 3/046* (2013.01); *A61K 8/0295* (2013.01); *A61K 8/20* (2013.01); *A61K 8/466* (2013.01); *A61K 8/737* (2013.01); *A61Q 5/02* (2013.01); *A61Q 19/10* (2013.01); *C11D 1/10* (2013.01); *C11D 1/126* (2013.01); *C11D 1/28* (2013.01); *C11D 1/37* (2013.01); *C11D 1/83* (2013.01); *C11D 1/94* (2013.01); *C11D 17/0026* (2013.01); *A61K 2800/596* (2013.01)

(58) Field of Classification Search
USPC ............... 510/422, 130, 156, 424, 462, 474
See application file for complete search history.

(56) References Cited

U.S. PATENT DOCUMENTS

| | | | | |
|---|---|---|---|---|
| 5,234,619 | A | * | 8/1993 | Greene et al. ................. 510/131 |
| 5,294,363 | A | * | 3/1994 | Schwartz et al. ............. 510/153 |
| 5,415,810 | A | * | 5/1995 | Lee et al. ...................... 510/403 |
| 5,952,286 | A | | 9/1999 | Puvvada |
| 5,962,395 | A | * | 10/1999 | Puvvada et al. ............... 510/418 |
| 6,074,633 | A | | 6/2000 | Dubief et al. |
| 6,077,816 | A | * | 6/2000 | Puvvada et al. ............... 510/130 |
| 6,150,312 | A | | 11/2000 | Puvvada et al. |
| 6,294,179 | B1 | | 9/2001 | Lee et al. |
| 6,426,326 | B1 | | 7/2002 | Mitra et al. |
| 8,029,772 | B2 | * | 10/2011 | Frantz et al. ................ 424/70.21 |
| 2002/0071819 | A1 | | 6/2002 | Giles et al. |
| 2003/0171231 | A1 | | 9/2003 | Shana'a et al. |
| 2003/0180246 | A1 | | 9/2003 | Frantz et al. |
| 2003/0190302 | A1 | | 10/2003 | Frantz et al. |
| 2004/0146475 | A1 | | 7/2004 | Peffly et al. |
| 2005/0137101 | A1 | | 6/2005 | Margosiak et al. |
| 2005/0158270 | A1 | | 7/2005 | Frantz et al. |
| 2006/0002880 | A1 | | 1/2006 | Peffly et al. |
| 2006/0079415 | A1 | | 4/2006 | Kozubal et al. |
| 2006/0135627 | A1 | | 6/2006 | Frantz et al. |
| 2007/0081953 | A1 | | 4/2007 | Dahms |
| 2007/0105746 | A1 | | 5/2007 | Dahms et al. |
| 2008/0153727 | A1 | | 6/2008 | Tsaur |
| 2008/0153729 | A1 | | 6/2008 | Tsaur |
| 2008/0153730 | A1 | | 6/2008 | Tsaur |
| 2009/0062177 | A1 | | 3/2009 | Tsaur |
| 2009/0156450 | A1 | | 6/2009 | Tsaur |

FOREIGN PATENT DOCUMENTS

WO    2004/098548 A1    11/2004

\* cited by examiner

*Primary Examiner* — Ling Choi
*Assistant Examiner* — Thuy-Ai Nguyen

(57) ABSTRACT

An aqueous structured surfactant composition contains an anionic surfactant selected from isethionate surfactants, taurate surfactants, and sarcosinate surfactants, and mixtures thereof, and an electrolyte and is useful in personal care applications.

8 Claims, No Drawings

STRUCTURED SURFACTANT SYSTEM

FIELD OF THE INVENTION

This invention relates to surfactant compositions, more particularly to structured surfactant compositions.

BACKGROUND OF THE INVENTION

Structured surfactant compositions are liquid crystalline compositions that are useful in home care applications such as liquid detergents, laundry detergents, hard surface cleansers, dish wash liquids, and personal care formulations such as shampoos, body wash, hand soap, lotions, creams, conditioners, shaving products, facial washes, baby care formulations, skin treatments. Surfactants in the structured surfactant compositions exist in the form of lamellar phases that are planar and/or in the form of spherulites. Commonly, the surfactant phase is present as spherulites, i.e., lamellar droplets, dispersed in the aqueous phase. Spherulites consist of an onion-like configuration of concentric bi-layers of surfactant molecules, between which is trapped water or electrolyte solution. Exclusively planar lamellar surfactant phases or exclusively spherulite lamellar surfactant phases or the combination of both forms can co-exist in the same composition. Structured surfactant compositions are typically pumpable, non-Newtonian compositions that have the capacity physically to suspend water insoluble particles by virtue of the presence of these lamellar surfactant phases.

Structured surfactant systems based on anionic surfactants, more typically branched ($C_{10}$-$C_{22}$)alkyl alkali metal sulfates, such as sodium trideceth sulfate, are known. U.S. Pat. No. 6,150,312 discloses structured surfactant compositions that comprise sodium trideceth sulfate, a fatty acid or fatty acid ester, and a zwitterionic or amphoteric surfactant and provide enhanced freeze thaw stability. U.S. Patent Application Publication No. US2003/0180246 A1 discloses structured surfactant compositions that comprise an anionic surfactant and an alkanolamide. U.S. Patent Application Publication No. US2003/0190302 A1 discloses structured surfactant compositions that comprise an anionic surfactant and a cationic surfactant. U.S. Patent Application Publication No. US200610135627-A1 discloses structured surfactant compositions that comprise an anionic surfactant and an amine oxide.

SUMMARY OF THE INVENTION

In a first aspect, the present invention is directed to an aqueous structured surfactant composition, comprising, based on 100 parts by weight ("pbw") of the composition:
(a) from greater than 0 to about 40 pbw of a first anionic surfactant selected from isethionate surfactants, taurate surfactants, sarcosinate surfactants, and mixtures thereof,
(b) optionally, a second anionic surfactant selected from anionic surfactants other than isethionate surfactants, taurate surfactants, and sarcosinate surfactants,
(c) optionally, one or more surfactants selected from amphoteric surfactants, zwitterionic surfactants, and mixtures thereof, and
(d) optionally, one or more non-ionic surfactants, and
(e) optionally, one or more cationic surfactants,
wherein the total amount of surfactants (a), (b), (c), (d), and (e) is from about 10 to about 40 pbw, and
(f) from greater than 0 to about 30 pbw of electrolyte in an amount effective to, in combination with components (a), (b), (c), (d), and (e), provide a structured surfactant composition that comprises a surfactant phase having an ordered liquid crystal structure.

In a second aspect, the present invention is directed to an aqueous personal care composition, comprising, based on 100 pbw of the composition:
(a) from greater than 0 to about 40 pbw of a first anionic surfactant selected from isethionate surfactants, taurate surfactants, sarcosinate surfactants, and mixtures thereof,
(b) optionally, a second anionic surfactant selected from anionic surfactants other than isethionate surfactants, taurate surfactants, and sarcosinate surfactants,
(c) optionally, one or more surfactants selected from amphoteric surfactants, zwitterionic surfactants, and mixtures thereof, and
(d) optionally, one or more non-ionic surfactants, and
(e) optionally, one or more cationic surfactants,
wherein the total amount of surfactants (a), (b), (c), (d), and (e) is from about 10 to about 40 pbw, and
(f) from greater than 0 to about 30 pbw of electrolyte in an amount effective to, in combination with components (a), (b), (c), (d), (e), form a structured surfactant composition that comprises a surfactant phase having an ordered liquid crystal structure, and
(g) greater than 0 pbw of one or more personal care benefit agents.

In one embodiment, the presence of a surfactant phase having an ordered liquid crystal structure of the surfactant phase is indirectly demonstrated by showing that the structured surfactant composition has an opaque visual appearance and a yield strength of greater than 0 Pascals.

In one embodiment, the composition exhibits shear thinning viscosity

In one embodiment, the composition is capable of suspending insoluble or partially insoluble components.

DETAILED DESCRIPTION OF INVENTION AND PREFERRED EMBODIMENTS

As used herein, the term "surfactant" means a compound that reduces surface tension when dissolved in water.

The composition of the present invention comprises, alone, or, more typically, interspersed with an aqueous phase, an ordered liquid crystal surfactant phase, typically a lamellar liquid crystal surfactant phase, more typically a spherulitic lamellar liquid crystal surfactant phase.

In many cases, it is possible to directly demonstrate the presence of an ordered liquid crystal surfactant phase by the technique of "freeze-fracture microscopy" in which sample of the composition is frozen by exposure to low temperature, the frozen sample is fractured, and one or more of the fracture surfaces of the fractured frozen sample are examined under a microscope.

It is also possible to indirectly demonstrate the presence of an ordered liquid crystal surfactant phase through inference based on the unique combination of properties exhibited by a composition that comprises such a phase.

Due to the presence of the ordered liquid crystal surfactant phase, the composition of the present invention exhibits, on visual inspection, an opaque appearance. The composition of the present invention exhibits an opaque appearance in the absence, as well as in the presence, of water insoluble components, such as oils.

As used herein, the term "opaque" means not completely transparent to light and ranges from a hazy translucent appearance through a turbid appearance to a uniform, saturated white appearance. In one embodiment, the structured surfactant compound of the present invention ranges from a turbid appearance to a uniform, saturated white appearance.

Due to the presence of the ordered liquid crystal surfactant phase, the composition of the present invention exhibits a yield strength of greater than 0 Pascals. As used herein, "yield strength" refers to the magnitude of the applied force required to induce the composition to flow. In one embodiment, the composition exhibits a yield strength of greater than 0.1 Pascals ("Pa"), more typically from about 1 to about 100 Pa, and even more typically from about 1 to about 10 Pa, as determined by measurements using a controlled stress/strain rheometer at two or more shear rates. The presence or absence of a non-zero yield strength may also be reliably determined on a qualitative basis by visual observation of the flow characteristics of the composition and the resistance of the composition to deformation caused by, for example, movement of a hand-held spatula a sample of the composition.

In one embodiment, the composition of the present invention is capable of suspending water insoluble or partially water-soluble components. The ability to suspend such components may be viewed as one manifestation of the presence of a non-zero yield strength.

As used herein in reference to a component of an aqueous composition, the terminology "water insoluble or partially water-soluble components" means that the component is present in the aqueous composition at a concentration above the solubility limit of the component so that, in the case of a water insoluble component, the component remains substantially non-dissolved in the aqueous composition and, in the case of a partially water-soluble component, at least a portion of such component remains undissolved in the aqueous composition. The water insoluble or partially water-soluble components may, for example, be in the form of solid particles, of continuous or discontinuous liquid phases, such as oil droplets, or of discontinuous gas phases, such as air bubbles.

As used herein, characterization of an aqueous composition as "capable of suspending", or as being "able of suspend" water insoluble or partially water-soluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition. The ability to suspend water insoluble or partially water-soluble components is one manifestation of the non-zero yield strength of the present invention, that is, the resistance of the structured surfactant composition of the present invention to deformation at low stresses is sufficient to balance the gravitational forces acting on water insoluble or partially water-soluble components, so that the components remain suspended in the structured surfactant composition.

In one embodiment, the presence of the ordered liquid crystal surfactant phase in the composition of the present invention is demonstrated by showing that the combined water, surfactant, and electrolyte components of the composition exhibit, in the presence and, more importantly, in the absence of water soluble components, an opaque visual appearance and exhibit a yield strength of greater than 0 Pascals.

As discussed above, the ordered liquid crystal phase, alone or more usually interspersed with an aqueous phase, provides a rheology which is sufficient, when the system is at rest, to immobilize any suspended particles but, upon application of a shearing force, is sufficiently low to allow the system to be pumped like a normal liquid. Such systems may display very low apparent viscosities when stirred, pumped or poured and yet be capable of maintaining particles, sometimes of millimeter or larger size, in suspension.

In one embodiment, the composition of the present invention exhibits shear-thinning viscosity. As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein, an indication that a composition is "substantially free" of a specific material, means that the composition contains no more than an insubstantial amount of that material, and an "insubstantial amount" means an amount that does not measurably affect the desired properties of the composition.

As used herein, an indication that a composition is "free" of a specific material, means that the composition contains no measurable amount of that material.

As used herein, the term "alkyl" means a monovalent saturated straight chain, branched or cyclic hydrocarbon radical, typically a monovalent saturated ($C_1$-$C_{20}$) hydrocarbon radical, such as for example, methyl, ethyl, n-propyl, iso-propyl, n-butyl, sec-butyl, t-butyl, pentyl, n-hexyl, cyclohexyl, and cyclooctyl, which may optionally be substituted on one or more of the carbon atoms of the radical. In one embodiment, an alkyl radical is substituted on one or more carbon atoms of the radical with hydroxy, alkoxy, amino, halo, carboxy, or phosphono, such as, for example, hydroxymethyl hydroxyethyl, methoxymethyl, ethoxymethyl, isopropoxyethyl, aminomethyl, chloromethyl or trichloromethyl, carboxyethyl, or phosphonomethyl.

As used herein, "alkylene" means a bivalent saturated straight chain, branched or cyclic hydrocarbon radical, typically a bivalent saturated ($C_1$-$C_{20}$) hydrocarbon radical, such as for example, methylene, dimethylene.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkenyl" means an unsaturated straight chain, branched chain, or cyclic hydrocarbon radical that contains one or more carbon-carbon double bonds, such as, for example, ethenyl, 1-propenyl, or 2-propenyl, which may optionally be substituted on one or more of the carbon atoms of the radical.

As used herein, the term "aryl" means a monovalent unsaturated hydrocarbon radical containing one or more six-membered carbon rings in which the unsaturation may be represented by three conjugated double bonds, such as for example, phenyl, naphthyl, anthryl, phenanthryl, or biphenyl, which may optionally be substituted one or more of carbons of the ring. In one embodiment, an aryl radical is substituted on one or more carbon atoms of the radical with hydroxy, alkenyl, halo, haloalkyl, or amino, such as, for example, methylphenyl, dimethylphenyl, hydroxyphenyl, chlorophenyl, trichloromethylphenyl, or aminophenyl.

As used herein, the term "aralkyl" means an alkyl group substituted with one or more aryl groups, such as, for example, phenylmethyl, phenylethyl, or triphenylmethyl, which may optionally be further substituted on one or more of the carbon atoms of the radical.

As used herein, the term "alkaryl" means an aryl group substituted with one or more alkyl groups, such as, for example, methylphenyl, dimethylphenyl, or trimethylphenyl, which may optionally be further substituted on one or more of the carbon atoms of the radical.

As used herein, the term "heterocyclyl" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the indication that a radical may be "optionally substituted" or "optionally further substituted" means, in general, that is unless further limited, either explicitly or by the context of such reference, that such radical may be substituted with one or more inorganic or organic substituent groups, such as, for example, alkyl, alkenyl, aryl, aralkyl, alkaryl, a hetero atom, or heterocyclyl, or with one or more functional groups that are capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, the terminology "$(C_x—C_y)$" in reference to an organic group, wherein x and y are each integers, indicates that the group may contain from x carbon atoms to y carbon atoms per group.

In one embodiment, the aqueous structured surfactant and/or personal care compositions of the present invention each comprise, based on 100 parts by weight of the composition:
(a) from greater than 0 to less than 40 pbw of the first anionic surfactant,
(b) from greater than 0 to about 20 pbw of the second anionic surfactant,
(c) from greater than 0 to about 25 pbw of one or more surfactants selected from amphoteric surfactants, zwitterionic surfactants, and mixtures thereof, and
(d) from greater than 0 to about 30 pbw of electrolyte in an amount effective to, in combination with components (a), (b), and (c), provide a structured surfactant composition having an opaque visual appearance and exhibiting a yield strength of greater than 0 Pascals.

In one embodiment, the total amount of surfactants the aqueous structured surfactant and/or personal care compositions of the present invention consists essentially of the first anionic surfactant, the second anionic surfactant, and the one or more surfactants selected from amphoteric surfactants, zwitterionic surfactants, and mixtures thereof. In one embodiment, the total amount of surfactants the aqueous structured surfactant and/or personal care compositions of the present invention consists of the first anionic surfactant, the second anionic surfactant and the one or more surfactants selected from amphoteric surfactants, zwitterionic surfactants, and mixtures thereof.

In another embodiment, the aqueous structured surfactant and/or personal care compositions of the present invention each comprise, based on 100 pbw of the composition:
(a) from greater than 0 to less than 40 pbw of the first anionic surfactant, and
(b) from greater than 0 to about 20 pbw of the second anionic surfactant selected from anionic surfactants other than isethionate surfactants, taurate surfactants, and sarcosinate surfactants, and
(c) from greater than 0 to about 30 pbw of electrolyte in an amount effective to, in combination with components (a) and (b), provide a structured surfactant composition having an opaque visual appearance and exhibiting a yield strength of greater than 0 Pascals.

In one embodiment, the total amount of surfactants the aqueous structured surfactant and/or personal care compositions of the present invention consists essentially of the first anionic surfactant and the second anionic surfactant. In one embodiment, the total amount of surfactants the aqueous structured surfactant and/or personal care compositions of the present invention consists of the first anionic surfactant and the second anionic surfactant.

In another embodiment, the aqueous structured surfactant and/or personal care compositions of the present invention each comprise, based on 100 pbw of the composition:
(a) from greater than 0 to less than 40 pbw of the first anionic surfactant, and
(b) from greater than 0 to about 25 pbw of one or more surfactants selected from amphoteric surfactants, zwitterionic surfactants, and mixtures thereof, and
(c) from greater than 0 to about 30 pbw of electrolyte, in an amount effective to, in combination with components (a) and (b), provide a structured surfactant composition having an opaque visual appearance and exhibiting a yield strength of greater than 0 Pascals.

In one embodiment, the total amount of surfactants the aqueous structured surfactant and/or personal care compositions of the present invention consists essentially of the first anionic surfactant and the one or more surfactants selected from amphoteric surfactants, zwitterionic surfactants, and mixtures thereof. In one embodiment, the total amount of surfactants the aqueous structured surfactant and/or personal care compositions of the present invention consists of the first anionic surfactant and the one or more surfactants selected from amphoteric surfactants, zwitterionic surfactants, and mixtures thereof.

In another embodiment, the aqueous structured surfactant and personal care compositions of the present invention each comprise, based on 100 pbw of the composition:
(a) from about 10 to about 40 pbw of the first anionic surfactant, and
(b) from greater than 0 to about 30 pbw of electrolyte in an amount effective to, in combination with component (a), provide a structured surfactant composition having an opaque visual appearance and exhibiting a yield strength of greater than 0 Pascals.

In one embodiment, the aqueous structured surfactant and/or personal care composition of the present invention each comprise, based on 100 pbw of the composition, from about 10 to about 90 pbw, more typically from about 20 to about 80 pbw, water.

In one embodiment, the total amount of surfactants the aqueous structured surfactant and/or personal care compositions of the present invention consists essentially of the first anionic surfactant. In one embodiment, the total amount of surfactants the aqueous structured surfactant and/or personal care compositions of the present invention consists of the first anionic surfactant.

In one embodiment, the aqueous structured surfactant and/or personal care composition of the present invention each exhibit a pH of from about 2.8 to about 12, more typically from about 4 to about 10.0, and even more typically from about 5 to about 8.

Surfactants

In one embodiment, total amount of all surfactants, including all anionic surfactants, amphoteric/zwitterionic surfactants, non-ionic surfactants, and cationic surfactant, contained in the aqueous structured surfactant and/or personal care composition of the present invention is from about 10 pbw to about 40 pbw, more typically from about 15 pbw to about 30 pbw, and even more typically from about 15 pbw to about 25 pbw.

In one embodiment, total amount of all surfactants, including all anionic surfactants, amphoteric/zwitterionic surfactants, non-ionic surfactants, and cationic surfactant, contained in the aqueous structured surfactant and/or personal care composition of the present invention is about 20 pbw to about 40 pbw, more typically from about 30 pbw to about 40 pbw.

In one embodiment, total amount of all surfactants, including all anionic surfactants, amphoteric/zwitterionic surfactants, non-ionic surfactants, and cationic surfactant, contained in the aqueous structured surfactant and/or personal care composition of the present invention is from about 10 pbw to less than about 30 pbw, more typically from 10 pbw to less than about 20 pbw, of a total amount of all surfactants.

(a) Isethionates/Taurates/Sarcosinates

In one embodiment, the aqueous structured surfactant and/or personal care composition of the present invention each comprise, based on 100 pbw of the composition, from about 0.5 to about 40 parts pbw, more typically from about 2 to about 30 pbw, and still more typically from about 5 to about 25 pbw, of the first anionic surfactant.

In one embodiment, the amount of first anionic surfactant contained in the structured surfactant and/or personal care composition of the present invention is from greater than 0 to 100 percent by weight (wt %), more typically from about 20 to about 100 wt %, even more typically form about 30 to about 80 wt %, and still more typically from about 40 to about 70 wt %, of the total amount of surfactant contained in the structured surfactant and/or personal care composition of the present invention.

In one embodiment, the amount of first anionic surfactant contained in the structured surfactant and/or personal care composition of the present invention is from greater than 0 to less than 50 wt %, more typically from about 5 to about 45 wt %, of the total amount of surfactant contained in the structured surfactant and/or personal care composition of the present invention.

In one embodiment, the amount of first anionic surfactant contained in the structured surfactant and/or personal care composition of the present invention is from about 50 to 100 wt %, more typically from about 55 to about 95 wt %, of the total amount of surfactant contained in the structured surfactant and/or personal care composition of the present invention.

In one embodiment, the first anionic surfactant comprises one or more anionic surfactant selected from isethionate surfactant compounds, taurate surfactant compounds, and sarcosinate surfactant compounds, according to structure (1):

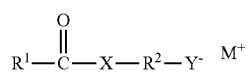

(1)

wherein:
R$^1$ is alkyl, alkenyl, aryl, or aralkyl,
R$^2$ is alkylene, which may optionally be substituted on one or more of such methylene units with alkyl, alkoxyl, alkenyl, aryl, aralkyl, alkaryl, or heterocyclyl, and which may optionally be interrupted at one or more positions by an oxygen atom,
X is O or NR$^3$,
NR$^3$ is H or alkyl,
Y$^-$ is SO$_3^-$ or CO$_2^-$, and
M$^+$ is a cation.

In one embodiment, R$^2$ is methylene, or dimethylene.

In one embodiment, R$^2$ is alkyleneoxyalkylene or alkylene poly(oxyalkylene) comprising from 2 to about 50 oxyalkylene units, more typically methylenepoly(oxyethylene), dimethylenepoly(oxyethylene), methylenepoly(oxypropylene), or dimethylenepoly(oxypropylene).

In one embodiment, M$^+$ is sodium, potassium, lithium, calcium, magnesium, ammonium cation, or an ammonium cation, such as, for example, an isopropylammonium, monoethanolammonium, diethanolammonium, or triethanolammonium cation. More typically, M+ is a sodium cation.

In one embodiment, the first anionic surfactant consists of a mixture of one or more isethionate surfactants and one or more taurate surfactants. In one embodiment, the first anionic surfactant consists of a mixture of one or more isethionate surfactants and one or more sarcosinate surfactants. In one embodiment, the first anionic surfactant consists of a mixture of one or more taurate surfactants and one or more sarcosinate surfactants. In one embodiment, the first anionic surfactant consists of a mixture of one or more isethionate surfactants, one or more taurate surfactants, and one or more sarcosinate surfactants.

In one embodiment, the first anionic surfactant comprises one or more isethionate surfactants. In one embodiment, the first anionic surfactant consists essentially of one or more isethionate surfactants. In one embodiment, the first anionic surfactant consists of one or more isethionate surfactants.

Suitable isethionate surfactants are esters of isethionic acid and salts thereof. In one embodiment, the first anionic surfactant comprises one or more isethionate surfactant compounds according to structure (2):

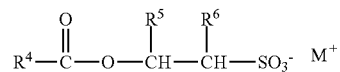

(2)

wherein:
R$^4$ is alkyl, alkenyl, aryl, or aralkyl,
R$^5$ and R$^6$ are each independently H or alkyl, and
M$^+$ is a cation.

In one embodiment, the first anionic surfactant comprises one or more N-acyl isethionate surfactant compounds according to structure (2), wherein R$^4$ is (C$_8$-C$_{22}$)alkyl and R$^5$ and R$^6$ are each independently H or (C$_1$-C$_4$)alkyl, more typically H or methyl.

In one embodiment, the first anionic surfactant comprises one or more N-acyl isethionate surfactant compounds according to structure (2), wherein R$^4$ is (C$_8$-C$_{22}$)alkyl and R$^5$ and R$^6$ are each independently H or (C$_1$-C$_4$)alkyl, more typically H or methyl, and M+ is a sodium, potassium, or ammonium cation.

Suitable isethionate surfactant compounds according to structure (2) include, for example, sodium lauroyl isethionate, sodium lauroyl isethionate, sodium myristoyl isethionate, sodium cocoyl isethionate, sodium oleoyl isethionate, and ammonium oleoyl isethionate.

In one embodiment, the first anionic surfactant comprises one or more taurate surfactants. In one embodiment, the first anionic surfactant consists essentially of one or more taurate surfactants. In one embodiment, the first anionic surfactant consists of one or more taurate surfactants.

Suitable taurate surfactants are amides of methyl taurine and salts thereof. In one embodiment, the first anionic surfactant comprises one or more taurate surfactant compounds according to structure (3):

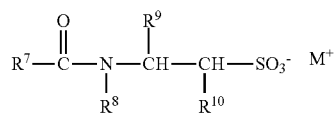

(3)

wherein:
R$^7$ is alkyl, alkenyl, aryl, or aralkyl
R$^8$ is H or alkyl,
R$^9$ and R$^{10}$ are each independently H or alkyl, and
M$^+$ is a cation.

In one embodiment, the first anionic surfactant comprises one or more N-acyl taurate surfactant compounds according to structure (3), wherein R$^7$ is (C$_8$-C$_{22}$)alkyl, R$^8$ is H or (C$_1$-C$_4$)alkyl, more typically H or methyl, and R$^9$ and R$^{10}$ are each independently H or (C$_1$-C$_4$)alkyl, more typically H or methyl.

In one embodiment, the first anionic surfactant comprises one or more N-acyl taurate surfactant compounds according to structure (3), wherein R$^7$ is (C$_8$-C$_{22}$)alkyl, R$^8$ is H or (C$_1$-C$_4$)alkyl, more typically H or methyl, and R$^9$ and R$^{10}$ are each independently H or (C$_1$-C$_4$)alkyl, more typically H or methyl, and M+ is a sodium, potassium, or ammonium cation.

Suitable taurate surfactant compounds according to structure (3) include, for example, sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate.

In one embodiment, the first anionic surfactant comprises one or more sarcosinate surfactants. In one embodiment, the first anionic surfactant consists essentially of one or more sarcosinate surfactants. In one embodiment, the first anionic surfactant consists of one or more sarcosinate surfactants.

Suitable sarcosinate surfactants are amides of sarcosine and salts thereof. In one embodiment, the first anionic surfactant comprises one or more sarcosinate surfactant compounds according to structure (4):

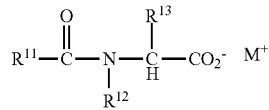

(4)

wherein:
R$^{11}$ is alkyl, alkenyl, aryl, or aralkyl, and
R$^{12}$ is H or alkyl,
R$^{13}$ is H, alkyl, and
M$^+$ is a cation.

In one embodiment, the first anionic surfactant comprises one or more sarcosinate surfactant compounds according to structure (4), wherein R$^{11}$ is (C$_8$-C$_{22}$)alkyl, and R$^{12}$ and R$^{13}$ are each independently H or (C$_1$-C$_4$)alkyl, more typically H or methyl.

In one embodiment, the first anionic surfactant comprises one or more sarcosinate surfactant compounds according to structure (4), wherein R$^{11}$ is (C$_8$-C$_{22}$)alkyl, R$^{12}$ and R$^{13}$ are each independently H or (C$_1$-C$_4$)alkyl, more typically H or methyl, and M+ is a sodium, potassium or ammonium cation.

Suitable sarcosinate surfactant compounds according to structure (4) include, for example, sodium lauroyl sarconsinate, sodium myristoyl sarconsinate, potassium myristoyl sarconsinate, sodium cocoyl sarconsinate, sodium oleoyl sarconsinate, triethanolamine lauroyl sarcosinate, and ammonium oleoyl sarconsinate.

The cationic counterion of any anionic surfactant in salt form is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts. Mixtures of the above cations are suitable as well.

(b) Anionics Other than Isethionate/Taurates/Sarcosinates

In one embodiment, the aqueous structured surfactant and/or personal care composition of the present invention each comprise, based on 100 pbw of the composition, from about 0.1 to about 20 pbw, more typically from about 0.1 pbw to about 15 pbw, and even more typically from about 0.5 pbw to about 10 pbw, of the anionic surfactant.

In one embodiment, the amount of second anionic surfactant contained in the structured surfactant and/or personal care composition of the present invention is from 0 to less than 100 wt %, more typically from 0 to about 80 wt %, even more typically form about 20 to about 70 wt %, and still more typically from about 30 to about 60 wt %, of the total amount of surfactant contained in the structured surfactant and/or personal care composition of the present invention.

In one embodiment, the amount of second anionic surfactant contained in the structured surfactant and/or personal care composition of the present invention is from 0 to less than about 50 wt %, more typically from about 5 to about 45 wt %, of the total amount of surfactant contained in the structured surfactant and/or personal care composition of the present invention.

In one embodiment, the amount of second anionic surfactant contained in the structured surfactant and/or personal care composition of the present invention is from 50 to less than 100 wt %, more typically from about 55 to about 95 wt %, of the total amount of surfactant contained in the structured surfactant and/or personal care composition of the present invention.

Suitable second anionic surfactants include, for example, alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, and dialkyl phosphates, alkyl lactylates, and salts thereof, as well as mixtures of such compounds.

In one embodiment, the second anionic surfactant comprises ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, disodium laureth sulfosuccinate, sodium monoalkyl phosphate, sodium dialkyl phosphate, ammonium cocoyl sulfate, sodium cocoyl sulfate, potassium cocoyl sulfate, monoethanolamine cocoyl sulfate, sodium tridecyl benzene sulfonate, and sodium dodecyl benzene sulfonate, or a mixture thereof.

In one embodiment, the second anionic surfactant comprises one or more branched and/or unsaturated anionic surfactants. Suitable branched anionic surfactants, include, for example, sodium trideceth sulfate, sodium tridecyl sulfate, ammonium trideceth sulfate, and ammonium tridecyl sulfate.

In one embodiment, the second anionic surfactant comprises one or more anionic organosulfate surfactants according to structure (5):

$$R^{14}-O-(C_mH_{2m}O)_n-SO_3^-X^+ \quad (5)$$

wherein
$R^{14}$ is $(C_8-C_{18})$alkyl or $(C_8-C_{18})$alkenyl, more typically $(C_{10}-C14)$alkyl,
m is 2, 3, or 4,
n is an integer of from 1 to about 7, more typically from 1 to 8, even more typically from 1 to 6,
$X^+$ is a cation.

In one embodiment, $R^{14}$ is a branched $(C_8-C_{18})$alkyl group or a $(C_8-C_{10-16})$alkenyl group, more typically a branched $(C_{10}-C_{16})$alkyl group, such as tridecyl.

Suitable branched alkyl groups include methyldecyl groups, methylundecyl groups, methyldodecyl groups, ethyldecyl groups, ethylundecyl groups, and ethyldodecyl groups, such as for example, 1-methyldecyl, 1-methylundecyl, 1-methyldodecyl, 1-ethyldecyl, 1-ethylundecyl, and 1-ethyldodecyl.

In one embodiment, m is 2 or 3, more typically 2.

In one embodiment, n is 1, 2, 3, or 4. As used herein, modifying an alkyl or alkenyl group with the suffix "eth" generally indicates the addition of one or more ethylene oxide units, for example, trideceth refers to an ethoxylated tridecyl group, and the suffix "-n", wherein n is an integer, indicates the number of such ethylene oxide units per group, for example "trideceth-3" indicates an ethoxylated tridecyl group with 3 ethylene oxide units per tridecyl group.

In one embodiment, the anionic organosulfate surfactant comprises one or more compounds selected from sodium laureth sulfates, potassium laureth sulfates, magnesium laureth sulfates, ammonium laureth sulfates, monoethanolamine laureth sulfates, diethanolamine laureth sulfates, triethanolamine laureth sulfates, sodium trideceth sulfates, magnesium trideceth sulfates, ammonium trideceth sulfates, monoethanolamine trideceth sulfates, diethanolamine trideceth sulfates, and triethanolamine trideceth sulfates. sodium oleth sulfates, potassium oleth sulfates, magnesium oleth sulfates, ammonium oleth sulfates, monoethanolamine oleth sulfates, diethanolamine oleth sulfates, triethanolamine oleth sulfates.

In one embodiment, the anionic organosulfate surfactant comprises one or more branched alkylether sulfate selected from sodium trideceth-1 sulfate, potassium trideceth-1 sulfate, and ammonium trideceth-1 sulfate, sodium trideceth-2 sulfate, potassium trideceth-2 sulfate, and ammonium trideceth-2 sulfate, sodium trideceth-3 sulfate, potassium trideceth-3 sulfate, and ammonium trideceth-3 sulfate, sodium trideceth-4 sulfate, potassium trideceth-4 sulfate, and ammonium trideceth-4 sulfate.

In one embodiment, the aqueous structured surfactant and/or personal care composition of the present invention are each substantially free of anionic surfactants other than isethionate surfactants, taurate surfactants, and sarcosinate surfactants. In one embodiment, the aqueous structured surfactant and/or personal care composition of the present invention are each free of anionic surfactants other than isethionate surfactants, taurate surfactants, and sarcosinate surfactants.

(c) Amphoterics/Zwitterionics

In one embodiment, the aqueous structured surfactant and/or personal care composition of the present invention each comprise, based on 100 pbw of the composition, from about 0.1 to about 25 pbw, more typically, from about 0.5 to about 10 pbw, of one or more amphoteric surfactants and/or zwitterionic surfactants ("amphoteric/zwitterionic surfactants").

In one embodiment, the amount of one or more amphoteric/zwitterionic surfactants contained in the structured surfactant and/or personal care composition of the present invention is from 0 to less than 100 wt %, more typically from 0 to about 80 wt %, even more typically form about 20 to about 70 wt %, and still more typically from about 30 to about 60 wt %, of the total amount of surfactant contained in the structured surfactant and/or personal care composition of the present invention.

In one embodiment, the amount of one or more amphoteric/zwitterionic surfactants contained in the structured surfactant and/or personal care composition of the present invention is from 0 to less than about 50 wt %, more typically from about 5 to about 45 wt %, of the total amount of surfactant contained in the structured surfactant and/or personal care composition of the present invention.

In one embodiment, the amount of one or more amphoteric/zwitterionic surfactants contained in the structured surfactant and/or personal care composition of the present invention is from 50 to less than 100 wt %, more typically from about 55 to about 95 wt %, of the total amount of surfactant contained in the structured surfactant and/or personal care composition of the present invention.

In one embodiment, the amphoteric/zwitterionic surfactant comprises derivatives of aliphatic secondary and tertiary amines in which the aliphatic radical is straight chain or branched and wherein one of the aliphatic substituents contains from about 8 to about 18 carbon atoms and one contains an anionic water-solubilizing group, as well as mixtures thereof.

Specific examples of suitable fatty acid amide amphoteric/zwitterionic surfactants include the alkali metal, alkaline earth metal, ammonium or substituted ammonium salts of alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropylsulfonate, caproamphodiacetate, caproamphoacetate, caproamphodipropionate, and stearoamphoacetate.

In one embodiment, the amphoteric/zwitterionic surfactant comprises sodium lauroamphoacetate, sodium lauroamphopropionate, disodium lauroamphodiacetate, sodium cocoamphoacetate, disodium cocoamphodiacetate, or a mixture thereof.

In one embodiment, the aqueous structured surfactant and/or personal care composition of the present invention are each substantially free of fatty acid amide amphoteric/zwitterionic surfactants. In one embodiment, the aqueous structured surfactant and/or personal care composition of the present invention are each free of fatty acid amide amphoteric/zwitterionic surfactants.

In one embodiment, the amphoteric/zwitterionic surfactant is selected from amphoteric/zwitterionic surfactants other than fatty acid amide amphoteric/zwitterionic surfactants.

Suitable amphoteric/zwitterionic surfactants other than fatty acid amide amphoteric/zwitterionic surfactants include, for example, fatty amine amphoteric/zwitterionic surfactants, and betaine surfactants, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, and lauryl bis-(2-hydroxy-ethyl)sulfopropyl betaine, and sultaine surfactants, such as alkylamidopropylhydroxy sultaines.

In one embodiment, the aqueous structured surfactant and/or personal care composition of the present invention are each substantially free of amphoteric/zwitterionic surfactants. In one embodiment, the aqueous structured surfactant and/or personal care composition of the present invention are each free of amphoteric/zwitterionic surfactants.

(d) Nonionics

In one embodiment, the aqueous structured surfactant and/or personal care composition of the present invention each comprise, based on 100 pbw of the composition, from about 0.1 to about 25 pbw, more typically, from about 0.5 to about 10 pbw, of one or more non-ionic surfactants.

In one embodiment, the amount of one or more nonionic surfactants contained in the structured surfactant and/or personal care composition of the present invention is from 0 to less than 100 wt %, more typically from 0 to about 80 wt %, even more typically form about 20 to about 70 wt %, and still more typically from about 30 to about 60 wt %, of the total amount of surfactant contained in the structured surfactant and/or personal care composition of the present invention.

In one embodiment, the amount of one or more nonionic surfactants contained in the structured surfactant and/or personal care composition of the present invention is from 0 to less than about 50 wt %, more typically from about 5 to about 45 wt %, of the total amount of surfactant contained in the structured surfactant and/or personal care composition of the present invention.

In one embodiment, the amount of one or more nonionic surfactants contained in the structured surfactant and/or personal care composition of the present invention is from 50 to less than 100 wt %, more typically from about 55 to about 95 wt %, of the total amount of surfactant contained in the structured surfactant and/or personal care composition of the present invention.

In one embodiment, the nonionic surfactant comprises one or more of alkanolamides, amine oxides, fatty alcohols, alkoxylated fatty alcohols, fatty acids, and fatty acid esters.

Suitable alkanolamides include aliphatic acid alkanolamides, such as cocamide DEA, cocamide MEA, cocamide MIPA, PEG-5 cocamide MEA, lauramide DEA, and lauramide MEA, as well as alkoxylated alkanolamides, and mixtures thereof.

Suitable amine oxides comprise, saturated or unsaturated branched or straight chain ($C_{10}$-$C_{24}$) alkyl dimethyl oxides or ($C_{10}$-$C_{24}$) alkyl amidopropyl amine oxides, such as for example, lauramine oxide, cocamine oxide, stearamine oxide, stearamidopropylamine oxide, palmitamidopropylamine oxide, decylamine oxide as well as mixtures thereof.

Suitable fatty alcohols include, for example, saturated or unsaturated branched or straight chain ($C_{10}$-$C_{24}$) alcohols, more typically saturated or unsaturated branched or straight chain ($C_{10}$-$C_{24}$) alcohols, such as for example, decyl alcohol, lauryl alcohol, myristyl alcohol, cetyl alcohol, stearyl alcohol, oleyl alcohol, linoleyl alcohol and linolenyl alcohol, and mixtures thereof.

Suitable alkoxylated fatty alcohols include alkoxylated, typically ethoxylated, derivatives of saturated or unsaturated branched or straight chain ($C_{10}$-$C_{24}$) alcohols, more typically saturated or unsaturated branched or straight chain ($C_{10}$-$C_{24}$) alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoylated alcohols may be used.

Suitable fatty acids include saturated or unsaturated ($C_{10}$-$C_{24}$) carboxylic acids, more typically saturated or unsaturated ($C_{10}$-$C_{24}$) carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof.

Suitable fatty acid esters include esters of saturated or unsaturated ($C_{10}$-$C_{24}$) carboxylic acids, more typically saturated or unsaturated ($C_{10}$-$C_{24}$) carboxylic acids, for example, propylene glycol isostearate, propylene glycol oleate, glyceryl isostearate, and glyceryl oleate, and mixtures thereof.

In one embodiment, the aqueous structured surfactant and/or personal care composition of the present invention are each substantially free of alkanolamides, amine oxides, fatty alcohols, alkoxylated fatty alcohols, fatty acids, and/or fatty acid esters. In one embodiment, the aqueous structured surfactant and/or personal care composition of the present invention are each free of alkanolamides, amine oxides, fatty alcohols, alkoxylated fatty alcohols, fatty acids, and/or fatty acid esters.

In one embodiment, the non-ionic surfactant is selected from non-ionic surfactants other than alkanolamides, amine oxides, fatty alcohols, alkoxylated fatty alcohols, fatty acids, and fatty acid esters.

Suitable non-ionic surfactants other than alkanolamides, amine oxides, fatty alcohols, alkoxylated fatty alcohols, fatty acids, and fatty acid esters include, for example, compounds produced by the condensation of alkylene oxide groups with an organic hydrophobic compound, which may be aliphatic, or alkyl aromatic in nature. Preferred nonionic surfactants consist of polyethylene, polypropylene, and polybutylene oxide condensates of alkyl phenols, and alkylpolyglycosides, and mixtures thereof.

In one embodiment, the aqueous structured surfactant and/or personal care composition of the present invention are each substantially free of nonionic surfactants. In one embodiment, the aqueous structured surfactant and/or personal care composition of the present invention are each free of nonionic surfactants.

(f) Cationics

In one embodiment, the aqueous structured surfactant and/or personal care composition of the present invention each comprise, based on 100 pbw of the composition, from about 0.1 to about 25 pbw, more typically from about 0.5 to about 10 pbw, of one or more cationic surfactants.

In one embodiment, the amount of one or more cationic surfactants contained in the structured surfactant and/or personal care composition of the present invention is from 0 to 10 wt %, more typically from about 0 to about 5 wt %, and even more typically from about 0 to about 3 wt % of the total amount of surfactant contained in the structured surfactant and/or personal care composition of the present invention.

Suitable cationic surfactants include for example, monocationic surfactants according to formula (6) below:

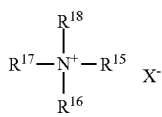

(6)

wherein:

$R^{15}$, $R^{16}$, $R^{17}$ and $R^{18}$ are each independently H or an organic group, provided that at least one of $R^{15}$, $R^{16}$, $R^{17}$ and $R^{18}$ is not hydrogen, and $X^-$ is an anion.

If one to three of $R^{15}$, $R^{16}$, $R^{17}$ and $R^{18}$ are each H, then the compound may be referred to as an amine salt. Some examples of cationic amines include polyethoxylated (2) oleyl/stearyl amine, ethoxylated tallow amine, cocoalkylamine, oleylamine, and tallow alkyl amine.

For quaternary ammonium compounds (generally referred to as quats) $R^{15}$, $R^{16}$, $R^{17}$ and $R^{18}$ may be the same or different organic group, but may not be hydrogen. In one embodiment, $R^{15}$, $R^{16}$, $R^{17}$ and $R^{18}$ are each independent ($C_8$-$C_{24}$) branched or linear hydrocarbon groups which may comprise additional functionality such as, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cataphyll morpholinium ethosulfate or steapyrium chloride.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2)hydroxyethyl ammonium dihydrogen phosphate (also known as hydroxyethyl cetyldimonium phosphate), babassuamidopropalkonium chloride, cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quatemium 80, Quaternium 82, Quaternium 84, behentrimonium chloride, dicetyl dimonium chloride, behentrimonium methosulfate, tallow trimonium chloride and behenamidopropyl ethyl dimonium ethosulfate. Mixtures may also be used in the present invention.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride, branched and/or unsaturated cationic surfactants such as isostearylaminopropalkonium chloride or olealkonium chloride, long chain cationic surfactants such as stearalkonium chloride and behentrimonium chloride, as well as mixtures thereof.

Suitable anionic counterions for the cationic surfactant include, for example, chloride, bromide, methosulfate, ethosulfate, lactate, saccharinate, acetate and phosphate anions.

In one embodiment, the aqueous structured surfactant and/or personal care composition of the present invention are each substantially free of cationic surfactants. In one embodiment, the aqueous structured surfactant and/or personal care composition of the present invention are each free of cationic surfactants.

(g) Electrolyte

In one embodiment, the aqueous structured surfactant and/or personal care composition of the present invention each comprise, based on 100 pbw of the composition, from greater than 0 to about 30 pbw, more typically from about 1 to about 20 pbw, still more typically from about 2 to about 10 pbw, still more typically from about 2 pbw to about 6 pbw, of an electrolyte.

In one embodiment, the aqueous structured surfactant and/or personal care composition of the present invention each comprise, based on 100 pbw of the composition, from greater than 0 to about 30 pbw, more typically from greater than 0 to about 20 pbw, still more typically from greater than 0.5 to about 10 pbw, still more typically from greater than 1.0 to about 8 pbw, of an electrolyte.

Suitable electrolytes include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulfonates, or naphthalene sulfonate formaldehyde copolymers.

Electrolyte may be added as a separate component or in combination with other components of the composition of the present invention.

The structured surfactant composition of the present invention may optionally further comprise one or more preservatives, such as benzyl alcohol, methyl paraben, propyl paraben, or imidazolidinyl urea, and DMDM hydantoin, and may optionally further comprise one or more pH adjusting agents, such as citric acid, succinic acid, phosphoric acid, sodium hydroxide, or sodium carbonate.

In general, the structured surfactant composition is made by combining and mixing the components in water, and optionally adjusting the pH and/or adding a preservative to the mixture.

The structured surfactant composition can also be subjected to high shear mixing. As used herein, the term "high shear mixing" refers to mixing under high shear conditions, typically at a shear rate of greater than or equal to about 1,000 $s^{-1}$, more typically greater than or equal to about 3,500 $s^{-1}$. The structured surfactant composition may be subjected to a high shear mixing in known mixing equipment, such as, for example, a high shear mixer or a homogenizer.

Viscosity is measured by known viscometric methods, such as for example, using a rotational viscometer, such as a Brookfield™ rotational viscometer, equipped with an appropriate spindle, at a rotation speed of from about 0.1 revolutions per minute ("rpm") to about 60 rpm.

In one embodiment, the aqueous structured surfactant and/or personal care composition of the present invention each exhibit a viscosity of greater than about 5,000 centipoise ("cp"), more typically greater than about 10,000 cp, when measured under relatively low shear conditions, for example, at 25° C. using a Brookfield™ rotational viscometer equipped with an RVT T-bar spindle and operated at 0.5 rpm.

In one embodiment, the aqueous structured surfactant and/or personal care composition of the present invention each exhibit a shear thinning behavior, wherein the viscosity under relatively high shear conditions, such as, for example, at 25° C. using a Brookfield™ rotational viscometer equipped with an RVT T-bar spindle and operated at 1 rpm is lower than the viscosity of the same composition measured under relatively low shear conditions by a factor of less than or equal to about 0.9, more typically less than or equal to about 0.7.

The composition of the present invention is capable of suspending water-insoluble particles or partially water-soluble components, such as vegetable oils, hydrocarbon oils, silicone oils, solid particles, abrasives, and similar articles. The composition provides a means to include otherwise difficult to incorporate components in surfactant mixtures resulting in cosmetic preparations with multi-functional benefits including, in some cases, cleansing, moisturizing, improved skin feel, exfoliation/abrasion, novel appearance, or a combination of these benefits.

The ability of a composition to suspend water insoluble or partially water-soluble components is typically evaluated by mixing the composition with sufficient vigor to entrap air bubbles in the composition and then visually observing whether the air bubbles remain entrapped in the composition for a defined period of time, such as for example, 12 to 24 hours, under defined environmental conditions, such as for example, room temperature. In one embodiment, the composition of the present invention is capable of suspending air bubbles for at least 1 week, and more typically for at least 3 months. A composition that is capable of suspending air bubbles for at least 12 hours at room temperature is deemed to be generally capable of suspending water insoluble or partially water-soluble components in the composition under generally anticipated processing, storage, and use conditions for such composition. For components other than air, the result of the air suspension test should be confirmed by conducting an analogous suspension test using the component of interest. For unusually rigorous processing, storage and/or use conditions, more rigorous testing may be appropriate.

In one embodiment, the ability to suspend water insoluble or partially water-soluble components is evaluated under more rigorous conditions, that is, the mixed samples are visually evaluated after subjecting the samples to one or more freeze/thaw cycles, wherein each freeze/thaw cycle consists of 12 hours at −10° C. and 12 hours at 25° C. In one embodiment, composition of the present invention remains capable of suspending air bubbles after one freeze/thaw cycle, more typically after 3 freeze/thaw cycles.

Personal Care Composition

The composition of the present invention is useful in, for example, personal care applications, such as shampoos, body wash, hand soap, lotions, creams, conditioners, shaving products, facial washes, neutralizing shampoos, personal wipes, and skin treatments, and in home care applications, such as liquid detergents, laundry detergents, hard surface cleansers, dish wash liquids, toilet bowl cleaners, as well as other applications, such as oil field and agrochemical applications.

In one embodiment, the personal care composition of the present invention comprises, based on 100 pbw of the composition, up to about 80 pbw, of one or more "benefit agents" that is, materials that provide a personal care benefit, such as moisturizing or conditioning, to the user of the personal care composition, such as, for example, emollients, moisturizers, conditioners, polymers, vitamins, abrasives, UV absorbers, antimicrobial agents, anti-dandruff agents, fragrances, sensory agents, and/or appearance modifying additives, such as, for example, colored particles or reflective particles, which may be in the form of a solid, liquid, or gas and may be insoluble or are only partly soluble in the structured surfactant composition. Mixtures of the benefit agents may be used.

Suitable benefit agents include, for example, oils, clays such as bentonite, kaolin, montmorillonite, sodium magnesium silicate, hectorite, magnesium aluminum silicate (Veegum), hydrocolloids such as agar, alginate, arabinoxylan, carrageenan, cellulose such as carboxyalkyl celluose, hydroxyalkyl cellulose, hydroxyalkyl alkyl cellulose, alkyl cellulose, curdlan, gelatin, gellan, β-glucan, guar gum, gum arabic, locust bean gum, pectin, starch, succinoglycan, xanthan gum, modified or substituted hydrocolloids such as hydroxy methyl cellulose, PG-hydroxyethyl cellulose, quaternary ammoniums of hydroxyethylcellulose, quaternary ammoniums of guar gum (Jaguar C-17, Jaguar C-14S, Jaguar Excel, Jaguar C-162 from Rhodia), hydroxypropyl guars (Jaguar HP-8, Jaguar HP-105, Jaguar HP-60, Jaguar HP-120, Jaguar C-162), modified starches such as sodium hydroxypropyl starch phosphate (Pure-Gel 980 and Pure-Gel 998 from Grain Processing Corporation), potato starch modified (Structure-Solanance from National Starch), acrylate copolymers such as Acrylates/Aminoacrylates/C10-30 Alkyl PEG-20 Itaconate Copolymer (Structure-Plus from National Starch), cationic polymers (Rheovis CSP, Rheovis CDE, Rheovis CDP from Ciba), polyacrylimidomethylpropane sulfonate/Polyquaternium-4 (Plexagel ASC from ISP), hydrophobically modified nonionic polyols (Acusol 880, Acusol 882 from Rohm & Haas), and PEG-150 Distearate, fragrances, sensory agents, such as camphor or menthol, anti-dandruff agents, and UV absorbing agents.

In one embodiment, the personal care composition of the present invention comprises, based on 100 pbw of the composition, from greater than 0 pbw to about 70 pbw, more typically from about 0.5 to about 70 pbw, even more typically from about 1 to about 50 pbw, still more typically from about 5 to about 40 pbw, most typically from about 10 to about 30 pbw of one or more oils.

Suitable oils include skin conditioning oils, such as, for example, vegetable oils, including arachis oil, castor oil, cocoa butter, coconut oil, corn oil, cotton seed oil, olive oil, palm kernel oil, rapeseed oil, safflower seed oil, sesame seed oil, and soybean oil, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and animal fats, including acetylated lanolin alcohols, lanolin, lard, mink oil, and tallow, hydrocarbon oils, such as petrolatum, and silicone oils, such as polydimethylsiloxane oils.

The personal care composition according to the present invention may optionally further comprise, based on 100 pbw of the personal care composition and independently for each such ingredient, up to about 10 pbw, typically from 0.5 pbw to about 5.0 pbw, of other ingredients in addition to benefit agents, such as, for example, preservatives such as benzyl alcohol, methyl paraben, propyl paraben and imidazolidinyl urea, electrolytes, such as sodium chloride, sodium sulfate, polyvinyl alcohol, and sodium citrate, pH adjusting agents such as citric acid, succinic acid, phosphoric acid, sodium hydroxide, sodium carbonate, dyes, and sequestering agents such as disodium ethylenediamine tetra-acetate. Other additional optional components are known in the art. For example, the CTFA Cosmetic Ingredient Handbook, Seventh Edition, 1997 and the Eighth Edition, 2000 describes a wide variety of cosmetic and pharmaceutical ingredients commonly used in personal care compositions, which are suitable for use in the compositions of the present invention.

In one embodiment, the personal care composition of the present invention comprises an aqueous structured surfactant component according to the present invention that forms a first "phase" (which may itself comprise a plurality of phases, including aqueous phases, planar lamellar surfactant phases and spherulitic lamellar surfactant phases, as discussed above) and the composition further comprises one or more additional phases that are at least substantially distinct from such first phase. As used herein in reference to the phases of a multiphase embodiments of the present invention, the terminology "substantially distinct" means that the phases each exhibit substantially homogeneous properties within a given phase and that the phases differ with respect to at least one characteristic or property, such as for example, visual characteristics, such as color, clarity, pearlescence, or physical/chemical properties, such as viscosity, lubricity, and/or benefit agent content.

The composition of the present invention may further comprise water-insoluble particles or partially insoluble components.

In one embodiment, a structured surfactant composition according to the present invention is a personal care composition selected from skin cleansers, such as hand soaps and body washes, and shampoos.

In one embodiment, the personal care composition of the present invention is a skin cleansing composition wherein the personal care benefit agent comprises one or more hydrocolloid polymers, one or more skin conditioning oils, or one or more hydrocolloid polymers and one or more skin conditioning oils.

In one embodiment, the personal care composition of the present invention is a skin cleansing composition wherein the composition comprises, based on 100 pbw of the composition, up to about 2 pbw, more typically from about 0.1 pbw to about 1 pbw, of a benefit agent selected from hydrocolloid polymers and mixtures thereof.

In one embodiment, the personal care composition of the present invention is a skin cleansing composition wherein the composition comprises, based on 100 pbw of the composition, from about 1 pbw to about 40 pbw, more typically from about 2 pbw to about 30 pbw, of a benefit agent selected from skin conditioning oils and mixtures thereof.

In one embodiment, the personal care composition of the present invention is a skin cleansing composition wherein the composition comprises, based on 100 pbw of the composition, up to about 2 pbw, more typically from about 0.1 pbw to about 1 pbw, of a benefit agent selected from hydrocolloid polymer and mixtures thereof, and from about 1 pbw to about 40 pbw, more typically from about 5 pbw to about 25 pbw, of a benefit agent selected from skin conditioning oils and mixtures thereof.

Suitable hydrocolloids include those described above in the general discussion of benefit agents. In one embodiment, the hydrocolloid polymer is selected from polysaccharide hydrocolloid polymers and derivatives of polysaccharide hydrocolloid polymers, including cationic derivatives of polysaccharide hydrocolloid polymers. Suitable polysaccharide hydrocolloid polymers and derivatives include guar gums, guar gum derivatives, such as hydroxypropyl trimethylammonium guar, hydroxypropyl lauryldimethylammonium guar, hydroxypropyl stearyldimethylammonium guar, hydroxypropyl guar, and carboxymethyl guar, xanthan gums, xanthan gum derivatives, starches, starch derivatives, and mixtures thereof.

Suitable skin conditioning oils include those described above in the general description of benefit agents and suitable oils. In one embodiment, the skin conditioning oil component of the skin cleansing composition comprises rape seed oil, soybean oil, shea butter, safflower oil, petrolatum, a silicone oil, or a mixture thereof.

In one embodiment, the personal care composition of the present invention is a shampoo composition wherein the personal care benefit agent comprises one or more hair conditioning oils, one or more hair benefit agents other than a hair conditioning oil, or one or more hair conditioning oils one and more hair benefit agents other than a hair conditioning oil.

In one embodiment, the personal care composition of the present invention is a shampoo composition that comprises, based on 100 pbw of the shampoo composition, from about 0.1 pbw to about 20 pbw, more typically from about 0.5 pbw to about 15 pbw, of a benefit agent selected from hair conditioning oils and mixtures thereof.

In one embodiment, the personal care composition of the present invention is a shampoo composition that comprises, based on 100 pbw of the shampoo composition, from about 0.01 pbw to about 5 pbw of benefit agent selected from hair benefit agents other than hair conditioning oils and mixtures thereof.

In one embodiment, the personal care composition of the present invention is a shampoo composition that comprises, based on 100 pbw of the shampoo composition, from about 0.1 pbw to about 20 pbw, more typically from about 0.5 pbw to about 15 pbw, of a benefit agent selected from hair conditioning oils and mixtures thereof, and from about 0.01 pbw to about 5 pbw of a benefit agent selected from hair benefit agents other than a hair conditioning oils and mixtures thereof.

Suitable hair conditioning oils are oils that remain fluid at room temperature, are dispersible, are neither irritating, toxic nor otherwise harmful when applied to the hair, are compatible with the other components of the shampoo composition, are chemically stable under normal use and storage conditions, and are capable of being deposited on and conditioning the hair, and include hydrocarbon oils, fatty acid derivative oils, fatty alcohol derivative oils, ester oils, poly α-olefin oils, silicone oils, and mixtures thereof. In one embodiment, the hair conditioning oil component of the shampoo composition comprises a silicone oil selected from alkyl and/or aryl substituted polysiloxane oils, such as polydimethylsiloxane, polydiethylsiloxane, and polymethylphenylsiloxane oils, polyalkyleneoxide-modified siloxanes, such as polypropylene oxide modified and polyethylene oxide modified polydimethylsiloxane oils, and amino- or amido substituted polysiloxane oils, such as amidodimethicone oil, as well as mixtures thereof.

Suitable hair benefit agents other than hair conditioning oils include, for example, anti-dandruff ingredients, and UV radiation absorbers. Suitable antidandruff agents include particulate, crystalline anti-dandruff agents, such as sulfur, selenium disulfide, and heavy metal salts of pyridinethione, such as zinc pyrithione, as well as soluble anti-dandruff agents, such as ketoconazole. Suitable UV radiation absorbers include, for example, sodium benzotriazolyl butylphenol sulfonate Examples 1 and 2

The compositions Examples 1-A and 2-A were made by mixing the listed ingredients in the relative amounts set forth in TABLE I below.

TABLE I

| Ingredient | Ex# 1-A (wt %) | EX# 2-A (wt %) |
|---|---|---|
| guar hydroxypropyl trimonium chloride | 0.5 | 0.5 |
| hydrogenated soy oil | — | 10 |
| sodium methyl cocoyl taurate | 2.88 | 2.88 |
| sodium cocoyl isethionate | 9.36 | 9.36 |
| sodium trideceth sulfate | 14.95 | 14.95 |
| sodium lauroamphoacetate | 2.88 | 2.88 |
| sodium xylene sulfonate | 0.24 | 0.24 |
| propylene glycol | 0.30 | 0.30 |
| DMDM hydantoin | 0.1 | 0.1 |
| Water | 68.78 | 58.78 |

The compositions of Examples 1-B to 1-D and 2-B to 2D were each made by adding ammonium chloride to one of the compositions of Examples 1-A and 2-A and adjusting the pH of the composition to 5.75. The viscosity of each of the compositions of Examples 1-A to 1-D and 2-A to 2-D was measured at 25° C. using a Brookfield™ rotational viscometer equipped with an RVT T-bar spindle and operated at 1 rpm and at 0.5 rpm. The relative amount of ammonium chloride (in percent by weight ("wt %"), based on the weight of the final composition) and the results of the viscosity measurements (in centiPoise ("cp")), and a visual observation regarding the appearance of the composition are given below in TABLE II for each of the compositions of Examples 1-A to 1-D and 2-A to 2-D.

TABLE II

| Ex# | NH₄Cl (wt %) | Viscosity at 1 rpm (cp) | Viscosity at 0.5 rpm (cp) | Appearance |
|---|---|---|---|---|
| 1-A | 0 | <15,000 | <15,000 | opaque, mobile |
| 1-B | 2 | 15,000 | 15,000 | opaque, semi-flowable |
| 1-C | 4 | 30,000 | 50,000 | opaque, semi-flowable |
| 1-D | 6 | 90,000 | 150,000 | opaque, semi-flowable |
| 2-A | 0 | <15,000 | <15,000 | opaque, mobile |
| 2-B | 2 | 110,000 | 180,000 | opaque, semi-flowable |
| 2-C | 4 | 170,000 | 310,000 | opaque, semi-flowable |
| 2-D | 6 | 140,000 | 280,000 | opaque, semi-flowable |

The stability of the compositions of Examples 1-A to 1-D and 2-A to 2-D was evaluated by visual observation of phase separation following conditioning of samples of those compositions at different temperatures. Samples of the compositions of Examples 1-A to 1-D were stored at room temperature. The samples of the compositions of Examples 1-A, 1-B, and 1-C separated within 24 hours of conditioning. The sample of the composition of Example 1-D separated within 3 days of conditioning.

Samples of the compositions of Examples 2-A to 2-D were stored at 4° C. and 45° C. The samples of the compositions of Examples 1-A and 1-D, C separated within 24 hours of conditioning. The samples of the compositions of Example 1-B and 1-C were stable after 6 weeks of conditioning.

Examples 3 to 6

The compositions Examples 3 to 6 were made by mixing the listed ingredients in the relative amounts set forth in TABLE III below.

TABLE III

| Ingredient | EX# 3 wt % | EX# 4 wt % | EX# 5 wt % | EX# 6 wt % |
|---|---|---|---|---|
| Water | 75.13 | 72.87 | 71.80 | 70.75 |
| sodium lauroamphoactetate | 5.38 | 5.22 | 5.14 | 5.07 |
| Sodium cocoyl n-methyl taurate | 10.21 | 9.90 | 9.75 | 9.61 |
| Sodium lauroyl-2-lactylate | 8.25 | 8.00 | 7.88 | 7.77 |
| Citric acid (50%) | 1.03 | 1.00 | 0.99 | 0.97 |
| NH₄Cl | 0.00 | 3.00 | 4.50 | 6.00 |
| Total | 100 | 100 | 100 | 100 |
| Appearance | 2-phase opaque/clear | 2-phase opaque/clear | 1-phase opaque | 1-phase opaque |
| Yield stress (Pa) | − | − | + | + |
| Viscosity (cPs), 12 rpm | − | − | 2900 | 3050 |

Each of the compositions of Examples 3-6 were visually evaluated with regard to the appearance and to the presence or absence of a non-zero yield strength. The viscosity of each of the compositions of Examples 5 and 6 was measured at 25° C. using a Brookfield™ rotational viscometer equipped with an LV3 spindle and operated at 12 rpm. Results of the visual evaluations for each of the compositions of Examples 3-6 and results of the viscosity measurements (in centipoise ("cp")) for the compositions of Examples 5 and 6 are given above in TABLE III.

The invention claimed is:

1. An aqueous personal care composition consisting of, based on 100 parts by weight of the composition:
   (a) from about 5 to about 25 parts by weight of a first anionic surfactant selected from isethionate surfactants, taurate surfactants, sarcosinate surfactants, and mixtures thereof,
   (b) from about 0.1 to about 20 parts by weight of a second anionic surfactant selected from anionic surfactants other than isethionate surfactants, taurate surfactants, and sarcosinate surfactants,
   (c) 0.5 to about 10 parts by weight of one or more surfactants selected from amphoteric surfactants, zwitterionic surfactants, and mixtures thereof, and
   (d) from 2 to about 6 parts by weight of electrolyte in an amount effective to, in combination with components (a), (b), and (c), provide a structured surfactant composition having an ordered liquid crystal structure and an opaque visual appearance and exhibiting a yield strength of greater than 0 Pascals,
   (e) up to about 2 parts by weight of a benefit agent selected from hydrocolloid polymers and mixtures thereof, and
   (f) from about 1 parts by weight to about 40 parts by weight, of a benefit agent selected from skin conditioning oils and mixtures thereof,
   (g) optionally from 0.5 to about 5.0 parts by weight of a pH adjusting agent,
   (h) optionally from 0.5 to about 5.0 parts by weight of a sequestering agent, and
   (i) water.

2. The composition of claim 1, wherein the first anionic surfactant is a mixture of an isethionate surfactant and a taurate surfactant.

3. The composition of claim 1, wherein the second anionic surfactant is a salt of tridecyl sulfate.

4. The composition of claim 1, wherein the one or more surfactants selected from amphoteric surfactants, zwitterionic surfactants, and mixtures thereof comprises a salt of lauroamphoacetate or lauroamphodiacetate.

5. The composition of claim 1, wherein the benefit agent selected from hydrocolloid polymers and mixtures thereof comprises a cationic derivative of a polysaccharide hydrocolloid polymer.

6. The composition of claim 1, wherein the first anionic surfactant comprises one or more isethionate surfactant compounds according to structure (2):

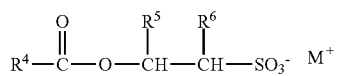
(2)

$R^4$ is $(C_8-C_{22})$alkyl, $R^5$ and $R^6$ are each independently H or $(C_1-C_4)$alkyl, and M+ is a sodium, potassium, or ammonium cation.

7. The composition of claim 1, wherein the first anionic surfactant comprises one or more taurate surfactant compounds according to structure (3):

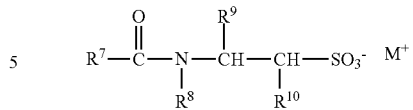
(3)

$R^7$ is $(C_8-C_{22})$alkyl, $R^8$ is H or $(C_1-C_4)$alkyl, $R^9$ and $R^{10}$ are each independently H or $(C_1-C_4)$alkyl, and M+ is a sodium, potassium, or ammonium cation.

8. The composition of claim 1, wherein the first anionic surfactant comprises one or more sarcosinate surfactant compounds according to structure (4):

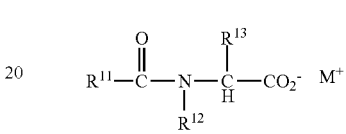
(4)

$R^{11}$ is $(C_8-C_{22})$alkyl, $R^{12}$ and R13 are each independently H or $(C_1-C_4)$alkyl, and M+ is a sodium, potassium or ammonium cation.

* * * * *